United States Patent [19]

Rosenberg et al.

[11] Patent Number: 5,089,398
[45] Date of Patent: Feb. 18, 1992

[54] ENHANCED YEAST TRANSCRIPTION EMPLOYING HYBRID GAPDH PROMOTER REGION CONSTRUCTS

[75] Inventors: Steven Rosenberg, Oakland; Patricia Tekamp-Olson, San Francisco, both of Calif.

[73] Assignee: Chiron Corporation, Emeryville, Calif.

[21] Appl. No.: 380,783

[22] Filed: Jul. 18, 1989

Related U.S. Application Data

[63] Continuation of Ser. No. 73,381, Jul. 13, 1987, abandoned, which is a continuation of Ser. No. 609,540, May 11, 1984, abandoned.

[51] Int. Cl.⁵ .................... C12P 21/00; C12P 7/00; C07H 15/12
[52] U.S. Cl. ..................... 435/69.1; 435/69.2; 435/69.3; 435/189; 435/192; 435/320.1; 435/255; 435/256; 435/172.3; 935/37; 536/27
[58] Field of Search .......... 435/69.1, 69.2, 69.4, 435/320.1, 212, 220, 172.3, 320, 255, 256, 189, 192; 935/37; 536/27

[56] References Cited

U.S. PATENT DOCUMENTS

4,615,974 10/1986 Kingsman et al. .................. 435/68

FOREIGN PATENT DOCUMENTS

0073635 3/1983 European Pat. Off. .
0073657 3/1983 European Pat. Off. .

OTHER PUBLICATIONS

Guarente et al., (1982) PNAS 79: 7410-4.
Tuite et al., (1982) EMBO 2: 603-8.
Miyanohara et al., (1983) PNAS 80: 1-5.
Kramer et al., (1984) PNAS 81: 367-70.
Sassone-Corsi et al., (1984) PNAS 81: 308-12.
Dobson et al., (1982) Nucleic Acids Res. 10: 2625-37.
Holland et al., (1979) J. Biol. Chem. 254: 5466-74.

*Primary Examiner*—Robin L. Teskin
*Attorney, Agent, or Firm*—Irell & Manella

[57] ABSTRACT

Yeast promoters of glycolytic enzymes are modified by isolating a fragment encompassing the RNA polymerase binding site and joining to the 5' end of this fragment a DNA sequence providing for enhanced inducible or constitutive transcription of a structural gene. Constructs are prepared for efficient expression of foreign genes in yeast.

Yeast strains 2150-2-3 (pC1/1GAPSOD) and AB110 (pC1/1GAPATi9), producing human $\alpha_1$-antitrypsin and superoxide dismutase, were desposited at the A.T.C.C. on May 9, 1984 and given Accession Nos. 20708 and 20709, respectively; and 2150-2-3 (GAP5), 2150-2-3 (Pyk5) and 2150-2-3 (PHO5GAP1), expressing Hepatitis B surface antigen, were deposited at the A.T.C.C. on May 9, 1984 and given Accession Nos. 20705, 20706 and 20707, respectively.

8 Claims, 3 Drawing Sheets

ENHANCED YEAST TRANSCRIPTION EMPLOYING HYBRID GAPDH PROMOTER REGION CONSTRUCTS

This application is a continuation of application Ser. No. 073,381, filed July 13, 1987 which is a continuation of U.S. Ser. No. 609,540 filed May 11, 1984, both now abandoned.

BACKGROUND OF THE INVENTION

1. Field of the Invention

With the advent of hybrid DNA technology, production of mammalian proteins in microorganisms became a reality. For the first time, mammalian proteins could be synthesized in a unicellular microorganism by introduction of a gene encoding for the mammalian protein under the transcriptional and translational control of regulator sequences recognized by the microorganism host. The introduction of these foreign constructions into a microorganism host resulted in competition between the regulator signals of the construct and the regulator signal endogenous to the host for the host systems involved with expression. The structural gene of interest is usually directed to a product which is nonproductive and may be injurious to the host. Therefore, host cells which can turn off the foreign gene can effectively dominate modified host cells.

Substantial progress has been made in isolating sequences concerned with transcriptional and translational regulation for protein expression. But frequently flanking sequences, as well as distance sequences, may also affect the efficiency and regulation of the expression of the protein. Therefore, as one manipulates these various sequences, removing them from their native environment, and joining them to unnatural sequences, that is sequences other than the wild-type sequence, one can never be certain as to the result.

In order to enhance the economies of producing proteins in microorganisms, there have been substantial efforts directed to improving the efficiency of transcription and translation, maximizing the proportion of total protein directed to production of the desired product, enhancing the viability of the modified host, as well as improving the efficiency with which the modified host may be obtained.

2. Description of the Prior Art

Guarente et al., *Proc. Natl. Acad. Sci. USA* (1982) 79:7410–7414, describes a hybrid promoter region employing the GAL4 regulatory region. Guarente and Ptashne, ibid. (1981) 78:2199–2203, report the presence of two domains in a yeast promoter, with a region upstream from the TATA sequence providing an activation site. Kramer et al., ibid. (1984) 81:367–370, describe the regulated expression of a human interferon gene in yeast employing the yeast acid phosphatase promoter, where expression is induced by phosphate or a temperature shift. Tekamp-Olson et al., Cold Spring Harbor Meeting, *Molecular Biology of Yeast*, 1983, describe the absence of deleterious effects on yeast viability when employing "short" promoters, as distinct from the presence of such effects, when employing an extended promoter region or "long" promoters.

SUMMARY OF THE INVENTION

Novel hybrid promoter regions are provided for use in conjunction with constructs having a structural gene under the transcriptional control of the hybrid promoter region and a terminator region. The hybrid promoter comprises a first segment providing transcriptional enhancement, either constitutive or regulated, and a second segment defining an RNA polymerase binding site and transcriptional initiation site. The hybrid promoter regions lack the deleterious effects associated with a wild-type promoter region in recombinant constructs, which results in reduced transformation efficiencies and lower yeast viability.

DESCRIPTION OF THE SPECIFIC EMBODIMENTS

Novel DNA fragments are provided as well as constructions employing the fragments for enhanced expression of structural genes in a yeast host. The constructs employing a hybrid promoter region provide for enhanced efficiencies of transformation and greatly improved viability of the yeast host as contrasted with those employing a wild-type yeast promoter. Concomitant with the improved viability is increased expression of a structural gene, in comparison with the truncated promoter region, and, therefore, greatly enhanced overall yields of expression products.

For the purposes of the subject invention, the "promoter region" is divided into two domains: (1) the structural gene proximal region, which includes the transcription initiation site, the "TATA" sequence, capping sequence, as appropriate, and an RNA polymerase binding sequence, which sequence intends a sequence which includes nucleotides upstream from the initiation site for directing the initiation of synthesis of the messenger RNA; and (2) a distal region which provides for regulated or constitutive expression, with enhanced expression as compared to the first domain linked to non-functional yeast DNA.

The hybrid promoters of the subject invention employ the RNA polymerase binding region of a yeast glycolytic enzyme promoter and a region upstream from said polymerase binding region, which is different from the wild-type upstream region of the RNA polymerase binding region and provides for enhanced efficiencies of transcription. This distal region will be derived from either a sequence, usually a yeast sequence, involved in regulation of transcription, or a prokaryotic sequence which provides for enhanced constitutive expression of the desired gene.

Conveniently, cassettes or constructs can be prepared which provide for one or more restriction sites intermediate the promoter region and a related terminator region where the structural gene may be inserted, so as to be under the transcriptional control of the hybrid promoter region. By having one or more restriction sites, one can provide for ease of insertion of the structural gene intermediate the transcription initiation and termination regions. The cassettes which can be prepared comprising the transcriptional initiation and termination region, having appropriate restriction sites for structural gene insertion can be cloned in prokaryotic vectors, so that after insertion of the structural gene, the resulting cassette, including the structural gene, may be cloned, isolated and purified, before introduction into a yeast vector.

The cassette, will for the most part, have the following formula:

-(P.R.(2)-P.R.(1))-R.S.-T.R.- wherein:

P.R.(1) is the promoter region proximal to the structural gene and having the transcription initiation site, the RNA polymerase binding site, and including the TATA box, the CAAT sequence, as well as translational regulatory signals, e.g., capping sequence, as appropriate;

P.R.(2) is the promoter region joined to the 5'-end of P.R.(1) associated with enhancing the efficiency of transcription of the RNA polymerase binding region;

R.S. is a sequence having one or more restriction recognition sites, preferably at least two restriction recognition sites, where the sites may result upon restriction into blunt ends or overhangs;

T.R. intends the termination region, which will include the terminator, which may be a stem and loop structure, and which may be associated with one or more stop codons, a polyadenylation signal sequence, if any, as well as any other transcriptional and translational termination sequences.

P.R.(1) will generally be at least about 150 bp, more usually at least about 200 bp, usually not more than about 600 bp, more usually not more than about 500 bp, generally not more than about 450 bp and preferably less than about 400 bp; the sequence will extend in the downstream direction of transcription to about bp +3, more usually bp −1 and may extend only to bp −20, more usually to bp −10 (the numbering intends that +1 is the first bp of the initiation codon with which the promoter region is associated in the wild-type host, while −1 is the immediately upstream bp and the integers increase in the direction of transcription;

P.R.(1) will be derived from a strong yeast promoter, normally a glycolytic enzyme promoter, such as glyceraldehyde-3-phosphate dehydrogenase, pyruvate kinase, alcohol dehydrogenase, phosphoglucoisomerase, triose phosphate isomerase, phosphofructokinase, etc.;

P.R.(2) will provide for an enhancing function of transcription, which enhancing function may provide for constitutive or regulated transcription; regulators will be derived from regions associated with regulation of yeast genes, other than the natural or wild-type gene associated with the first domain in the wild-type or natural host, such as UDP-galactose epimerase (GAL10), galactokinase (GAL1), acid phosphatase (PHO5), etc. For yeast regulatory sequences, the domain will usually be at least about 100 bp, more usually at least about 200 bp, for convenience generally not exceeding about 3 kbp, usually not exceeding about 1 kbp, desirably not exceeding about 600 bp. The regulatory region will generally begin at least about 200 bp from the initiation codon, usually at least about 300 bp and may begin at 400 bp or farther upstream from the initiation codon.

Regulation can be as a result of a change in the chemical or physical environment of the host, such as a change in carbon source, e.g., glucose to galactose or vice versa; a change in concentration of a nutrient, e.g., an inorganic nutrient such as a phosphate; or a change in temperature, e.g., 25° C. to 35° C. Constitutive transcription can be achieved employing prokaryotic sequences of at least about 500 bp, usually 1 kbp or more, for convenience, generally not exceeding about 5 kbp; conveniently, the prokaryotic sequence can be obtained from the vector in which the cassette is cloned, illustrative vectors including pBR322, lambda, Charon 4A, pACYC184, pUC5, etc.

R.S. will generally be at least 4 bp, more usually at least 6 bp, and may be 100 bp or more, more usually being not more than about 60 bp and may include one or more, usually not more than about 10 restriction sites, where such restriction sites may be illustrated by EcoRI, BamHI, SalI, HindIII, AluI, AvaI, TaqI, HpaI, etc., having at least one unique restriction site for the construct sequences.

T.R. is the termination region which will include the necessary transcriptional and translational signals for termination, such as the polyadenylation site, etc.;

T.R. will generally be at least about 100 bp, more usually at least 150 bp, and generally less than about 1 kbp, usually less than about 600 kbp; the termination region may be derived from any convenient yeast sequence, so long as the terminator balances the promoter, conveniently being derived from a glycolytic enzyme terminator, where the terminator may be associated with the same or different enzyme with which the promoter is associated.

Where a cassette is cloned in a bacterial vector, the construction will have the following formula:

$$\overline{[-(P.R.(2)-P.R.(1))-R.S.-T.R.-Rep(B)-(M(B))_a-]}_{(-)_b}$$

wherein all the symbols have been defined previously, except for:

Rep (B), which intends a replicon or replication system recognized by a prokaryotic host and may be derived from a plasmid or phage, such as ColE1, and R plasmid, e.g., pRK290, lambda, e.g., Charon 4A, λdv, etc.;

M is a marker which provides for selection of hosts containing the construction, where (B) intends a prokaryotic, e.g., bacterial, host and a intends an integer of from 0 to 3, usually 1 to 2, although additional markers may be present, where the marker allows for selection of the host containing the construct as well as providing for selective pressure on maintaining hosts having the construct; the markers include biocide resistance, such as antibiotic resistance, toxin resistance and heavy metal resistance; providing prototrophy to an auxotrophic host; providing immunity; and the like;

the markers may provide for complementation of an auxotrophic host, e.g., his$^-$, ura$^-$, trp$^-$, leu$^-$ genotype, resulting in prototrophy; resistance to metals, such as cup$^+$ genotype; resistance to antibiotics, such as amp$^r$, tc$^r$, cam$^r$, str$^r$, tur$^r$ genotype, etc.;

b is 0 or 1, intending that the construction is either linear or circular, usually circular.

The above construct can be used for insertion of a wide variety of structural genes, both prokaryotic and eukaryotic, both naturally occurring and synthetic, where the genes may include signal leaders for secretion, and the like. The genes may express enzymes, hormones, proteins from pathogens for vaccines, structural proteins, lymphokines, membrane surface proteins, immunoglobulins, blood proteins, or the like. The particular structural gene which is inserted is not critical to this invention and any polypeptide or protein of interest may be prepared employing the constructions of the subject invention. The structural genes will usually be foreign to the yeast host, where foreign intends different from wild-type yeast structural genes and from a source that does not normally exchange genetic information with yeast.

Usually, the structural gene will be at least about 36 bp, and not more than about 20 kbp, usually not more than about 3000 bp, usually not more than about 1500 bp. Included in the structural gene may be non-coding flanking regions, the 5'-flanking region normally being quite short, usually less than about 30 bp, while the 3'-flanking region may be extended, usually not exceeding about 500 bp. Thus, the structural gene fragment will usually include the translational stop codons for proper termination of amino acid chain extension.

When the structural gene has been inserted into the cassette which is joined to a yeast replication system, normally including one or more markers recognized by yeast, the resulting construct will have the following formula:

$$[(P.R.(2)-P.R.(1))-\text{gene}-T.R.-\text{Rep}(Y)-(M(Y))_a]$$

wherein all of the symbols have been defined previously except for:
gene, which intends the structural gene, having its initiation codon and stop codons as appropriate; and
Y, which intends that the symbol is related to yeast.

Convenient yeast replication systems include the 2 μm plasmid replication system, combination of CEN3 and ARS1 or ARS3, or the like. The replication systems may be high or low copy number, depending on the effect of the construct on the viability of the host. While the indicated replication systems are those which have found common employment, any replication system useful in yeast may be employed which provides for efficient replication and maintenance. Often the structural gene will be inserted into an appropriate shuttle vector capable of replication and selection in either a yeast or bacterial host, where the resulting construction will have the following formula:

$$[(P.R.(2)-P.R.(1))-\text{gene}-T.R.-\text{Rep}(Y)-(M(Y))_a-\text{Rep}(B)-(M(B))_a]$$

where all symbols have been defined previously. Also, it is, of course, understood that the cassette without an inserted structural gene but containing the restriction enzyme recognition sequence, R.S., may be propagated in yeast or contained within a shuttle vector, where the construction will have the following respective formulae:

$$[(P.R.(2)-P.R.(1))-R.S.-T.R.-\text{Rep}(Y)-(M(Y))_a]$$

$$[(P.R.(2)-P.R.(1))-R.S.-T.R.-\text{Rep}(Y)-(M(Y))_a-\text{Rep}(B)-(M(B))_a]$$

where all symbols have been defined previously.

The various fragments which form the cassette and final constructions may be joined together in accordance with conventional ways. In many cases, genes have been isolated and restriction mapped, as well as sequenced. To that extent, one can select the sequence of interest by restriction of the gene, employing further manipulation as necessary such as resection with Bal31, in vitro mutagenesis, primer repair, or the like, to provide a fragment of a desired size, including the desired sequence, and having the appropriate termini. Linkers and adapters can be used for joining sequences, as well as replacing lost sequences, where the restriction site is internal to the region of interest. The various fragments which are isolated, may be purified by electrophoresis, electroeluted, ligated to other sequences, cloned, reisolated and further manipulated.

The use of regulatory sequences for controlling transcription of the structural gene of interest allows for growing the host cells to high density with no or low levels of expression of the structural gene, and then inducing expression by changing the environmental conditions, e.g., nutrient, temperature, etc.

For example, with the GAL4 regulatory region, the yeast cells could be grown in rich media with a glycerol-lactic acid combination to high density, e.g., mid or late log phase, followed by switching the carbon source to galactose. For PHO5 regulation one could grow the cells at high phosphate, about 1 to 10 mM, and then decrease the phosphate concentration to about 0.1 to 0.5 mM. For temperature sensitivity, one could grow the cells at 25° to 37° C. and then change the temperature as appropriate by about 5° to 20° C. The host cells would have the regulatory system associated with the regulatory region employed.

Various techniques will be exemplified in the Experimental section of this application, which techniques can be used as paradigmatic for constructions employing fragments from sources other than those exemplified. Of particular interest, as evidenced by the Experimental section, will be the use of the glyceraldehyde-3-phosphate dehydrogenase promoter region for the RNA polymerase binding site in conjunction with regulator sequences, such as those associated with GAL4, PHO5, or the like. In referring to the GAL4 regulatory region or associated sequence, the region intends the sequence associated with regulation of other galactose metabolism genes, e.g., GAL1 and GAL10, which are under the regulatory control of such sequence in conjunction with the expression product of the GAL4 gene. The PHO5 sequence refers to a region associated with the PHO5 gene which provides for transcriptional regulation of the PHO5 gene.

The following examples are offered by way of illustration and not by way of limitation.

EXPERIMENTAL

All DNA manipulations were done according to standard procedures. See *Molecular Cloning*, T. Maniatis et al., Cold Spring Harbor Lab., 1982. Enzymes used in cloning were utilized as per the manufacturer's specifications. Enzymes were obtained either from New England Biolabs or Bethesda Research Laboratories. Procedures with these enzymes employed the supplier's directions. Yeast were transformed and grown using a variety of media including selective medium (yeast nitrogen base without leucine); YEPD medium, containing 1% (w/v) yeast extract, 2% (w/v) peptone and 2% (w/v) glucose, and others as appropriate and/or detailed below. Plating medium contained 2% (w/v) agar and for transformation 3% top agar. Hepatitis B surface antigen was determined after lysis of yeast by glass bead agitation and clarification by centrifugation, using the AusriaII assay (Abbott Laboratories). Protein is determined by the Coomassie dye binding method.

Construction of GAL Regulator Containing Plasmids

Plasmid pLGSD5 is prepared as described in Guarente et al., (1982) supra. The plasmid was manipulated as follows: After restriction with XhoI, the overhangs were filled in with the Klenow fragment of DNA polymerase I ("Klenow fragment"), ligated with EcoRI linkers (GGAATTCC) and then completely digested with EcoRI and Sau3A to provide a 370 bp fragment which was isolated by gel electrophoresis and included the intergenic sequence between GAL1 and GAL10 genes of yeast, and provides for the GAL4 regulation sequence of the GAL1 and GAL10 genes.

This fragment was inserted into pBR322 which had been completely digested with EcoRI and BamHI followed by treatment with alkaline phosphatase to prevent oligomerization. The resulting plasmid pBRGAL4 was treated in two different ways.

In the first procedure pBRGAL4 was completely digested with Sau3A, the overhangs filled in with the Klenow fragment, and the resulting blunt-ended fragment ligated with SalI linkers (CGTCGACG), followed by digestion with SalI and XhoI. The resulting 370 bp fragment was isolated by gel electrophoresis. This fragment has the original 370 bp yeast GAL4 regulator sequence with XhoI and SalI termini.

The second fragment was obtained by complete digestion of pBRGAL4 with XhoI and SalI to provide a XhoI-SalI fragment which included the 370 bp yeast GAL4 regulator sequence as well as about 280 bp of pBR322, the GAL4 sequence extending from Sau3A to SalI.

The two fragments were then cloned in the plasmid plot5. plot5 was prepared by inserting the 40 bp polylinker fragment of the following sequence

650 bp fragments independently inserted into plot5 to provide plasmids plot5GAL4/370 and plot5-GAL4/650, respectively. Each of the plasmids was then completely digested with BamHI and SalI to reproduce the individual fragments extended by 6 bp of the polylinker fragment. These fragments were then ligated into pCl/1, which had been completely digested with BamHI and SalI followed by treatment with alkaline phosphatase to prevent recircularization. Plasmid pCl/1 is a derivative of pJDB219 (Beggs, *Nature* (1978) 275:104) in which the region corresponding to bacterial plasmid pMB9 in pJDB219 has been replaced by pBR322 in pCl/1. The resulting plasmids were designated pCl/1GAL4/370 and pCl/1GAL4/650, respectively. The BamHI-SalI fragment is located in the pBR322 portion of the vector pCl/1.

The next construction develops a hybrid promoter for expression of the Hepatitis B surface antigen (HBsAg or sAg), employing the RNA polymerase binding region of GAPDH. The previously prepared plasmid pHBS56/16-3, a yeast shuttle vector containing the alcohol dehydrogenase 1 (ADH1) promoter, the HBsAg gene and ADH terminator as a SphI fragment, was digested with SphI and the ends modified with Bam linkers. The Bam linkers have the sequence CGGATCCG.

pHBS56/16-3 was prepared as follows: A TaqI-HpaI fragment obtained from the HBsAg coding region which included 26 bp of the pre-sAg region, 681 bp of the sAg region and 128 bp of the 3'-untranslated region, was linked with EcoRI linkers and cloned at the EcoRI site in pBR322. The EcoRI linkers have the sequence GGAATTCC. The plasmid pHBS5 was thus obtained.

After digesting pHBS5 with EcoRI, the digest was resected with Bal31 and religated with EcoRI linkers (GGAATTCC). After digestion with EcoRI the material of about 800 bp was isolated from a polyacrylamide gel. This isolate was then recloned into pBR322 which had been digested with EcoRI and treated with alkaline phosphatase. Where the resection was to the sequence CATGG, which included the methionine codon, the EcoRI linker created an NcoI site. The plasmids were screened for the presence of an NcoI site and one of the plasmids chosen for further manipulation. This plasmid, designated pHBS5-3, was restricted with EcoRI, the EcoRI fragment made blunt-ended with Klenow fragment and dNTPs, and the blunt-ended fragment was then restricted with XbaI to provide an about 100 bp fragment having an XbaI overhang and blunt end at the former EcoRI site.

pHBS5 was then digested with ClaI, made blunt-ended with the Klenow fragment and dNTPs, digested with XbaI, followed by alkaline phosphatase treatment. The 100 bp fragment was then inserted into the vector to provide the plasmid pHBS6. Upon sequencing of the into pBR322 as an EcoRI-PvuII substitution followed by insertion of the trp-lac promoter (Russell and Bennett, *Gene* (1982) 20:231-245) into the PvuII site with transcription oriented toward the polylinker sequence. plot5 was completely digested with SalI, followed by treatment with alkaline phosphatase and the 370 bp and blunt-ended ligation site, it was found that an adenosine had been lost, so as to lose the EcoRI site, where the sequence was now ATCGATTCCCATGG. The ClaI and NcoI sites were retained. The loss of the A resulted in pHBS6 having a single EcoRI site.

pHBS5-3 was digested with EcoRI and the resulting EcoRI fragment having the sAg fragment isolated by gel electrophoresis and inserted into the vector pHBS16 (Valenzuela et al., *Nature* (1982) 298:347-350). This plasmid has the ADH1 promoter and the sAg gene in an EcoRI fragment in a plasmid containing the 2 μm origin, a TrpI gene and pBR322. The plasmid was digested with EcoRI, treated with alkaline phosphatase to prevent recircularization, and the EcoRI fragment from pHBS5-3 inserted to provide pHBS16-3, where the sAg gene isolated as a TaqI-HpaI fragment had been modified by Bal31 resection. The plasmid pHBS16-3 was digested with SphI and XbaI to provide a fragment which had the ADH promoter at the Sph terminus and the 5'-end of the sAg gene.

pHBS56 was then digested with SphI. pHBS56 was prepared from pCl/1 by digestion with SphI, which deletes a portion of the plasmid spanning the 2 μm-pBR322 joint. The active portion of the ADH1 promoter region is contained within the SphI-HindIII fragment of approximately 300 bp (Bennetzen et al., *J. Biol. Chem.* (1982) 257:301). The SphI site in the ADH promoter begins at position −413 and the yeast terminator sequence is contained within a HindIII-SphI fragment of about 330 bp. In each case the SphI site is distal to the coding region. A 1500 bp ADH1 promoter fragment terminating at position −9 (Hitzeman et al., *Nature* (1981) 293:717) and an approximately 450 bp terminator unit from nucleotides 913 to 1368 in the ADH gene nucleotide sequence were joined at a HindIII site between the fragments and cloned into the BamHI site of the vector YEp13 (Broach and Hicks, *Gene* (1979) 8:121) to provide pADH5.

The HBsAg-DNA segment of pHBS5 was excised by EcoRI digestion, blunt-ended with the Klenow fragment and joined at both ends with HindIII linkers, CAAGCTTG. After digestion with HindIII, the HBsAg fragment was inserted into the HindIII site of the plasmid pADH5 which had been digested at the HindIII site intermediate the ADH1 promoter and terminator sequence. A plasmid with the HBsAg gene in the correct orientation as determined by restriction analysis was designated pHBS22. The cassette was included between two SphI restriction sites. pHBS22 was digested with SphI to obtain a fragment of about 1500 bp and inserted into SphI digested pCl/1 to provide pHBS56 which was cloned in *E. coli* HB101.

pHBS56 was digested with SphI and XbaI to provide a 1.1 kb fragment having the ADH terminator region and the 3'-portion of the sAg gene with the SphI site proximal to the terminator region. The 1.1 kb SphI-XbaI fragment was joined to the SphI-XbaI fragment from pHBS16-3, which resulted in providing the complete sAg gene in the correct orientation between the ADH promoter and terminator. This SphI-SphI fragment was then ligated to SphI digested pHBS56, replacing the cassette of pHBS56 to provide the plasmid pHBS56/16-3 with the resected sAg coding region fragment. The cassette was then excised from pHBS56/16-3 by digestion with SphI, followed by chewing back the overhangs with the Klenow fragment in the presence of dNTPs, then ligated with BamHI linkers, followed by digestion with BamHI to provide a 1.6 kb fragment which was isolated by gel electrophoresis. The fragment included the ADH promoter region, the sAg gene and ADH terminator region, as described above. This fragment was inserted into the BamHI site of pBR322 to provide pPGT16-3 which was digested with BamHI and XbaI and the resulting 1.1 kb fragment gel isolated, where the XbaI-BamHI fragment had the 3' portion of the sAg gene and the ADH terminator region.

pHBS6 was digested with XbaI and NcoI and the 94 bp fragment gel isolated to provide the 5'-portion of the sAg gene. A synthetic adapter was prepared of the formula having TaqI and NcoI termini and providing the −25 to −1 nucleotides of the GAPDH (GAP49) promoter and the initiation codon of the sAg gene. This synthetic fragment, the NcoI-XbaI fragment, and the XbaI-BamHI fragment were ligated simultaneously, followed by digestion with TaqI and BamHI. The resulting fragment was then substituted into pBR322 linearized with ClaI and BamHI, followed by treatment with alkaline phosphatase. The resulting plasmid, which contains the −1 to −25 bp of the GAPDH promoter region, the sAg gene, and the ADH terminator, where the NcoI restriction site is lost was called pHBS6LGAPsAg-tADH.

pGAP1, a plasmid prepared by insertion of a HindIII fragment containing the GAPDH gene GAP49 (Holland and Holland, *J. Biol. Chem.* (1979) 254:5466-5474) inserted in the HindIII site of pBR322, was digested with HinfI and a 500 bp promoter containing fragment isolated. The fragment was resected with Bal31 to remove about 50 or 90 bp, followed by ligation with HindIII linkers and digestion with HindIII. pBR322 was digested with HindIII, followed by treatment with alkaline phosphatase and the about 450 or 410 bp fragment inserted to provide pGAP128 and pGAP396, respectively.

pGAP128 was digested with HindIII, the fragment made blunt-ended with the Klenow fragment and dNTPs and the resulting 450 bp fragment isolated by gel electrophoresis. This fragment was inserted into SmaI digested plot5, which had been treated with alkaline phosphatase, to provide plasmid plot5pGAP128, which contained about −400 to +27 bp of the GAPDH promoter and coding region. Plasmid plot5-pGAP396 was prepared from pGAP396 in an identical manner and thus differs from plasmid plot5pGAP128 in having about 15-30 fewer bp at each terminus of the GAPDH promoter region (about −385 to −3).

Plasmids GAP1-GAP4 were then prepared in the following manner. Plasmid plot5pGAP128 was digested with TaqI and BamHI to provide an about 390 bp TaqI-BamHI fragment which included the −26 to about −400 bp of the GAPDH promoter region and a portion of the HindIII and plot5 polylinker. pHBS6LGAPsAgtADH plasmid was also digested with TaqI and BamHI and a 1.1 kb TaqI-BamHI fragment containing the 3'-terminus of the GAPDH promoter region, the sAg gene and the ADH terminator region was gel isolated and ligated to the other TaqI-BamHI fragment to provide a BamHI-BamHI fragment which included approximately 400 bp of the GAPDH promoter region, the sAg gene in proper orientation for transcriptional regulation by the GAPDH promoter, followed by the ADH terminator region. This fragment was ligated into pBR322 which had been digested with BamHI and treated with alkaline phosphatase to provide plasmid pPGT80. This BamHI cassette could now be isolated and inserted into plasmid pCl/1, at the BamHI site in the pBR322 portion of pCl/1, where in plasmid GAP1 the ADH terminator region is proximal to the amp' gene with the pBR322 portion divided into an approximately 4 kb sequence including the amp' gene and a 375 bp region separating the cassette from the 2 μm sequences. In GAP2, the promoter is adjacent to the long pBR322 sequence with transcription in the same direction as the amp' gene. The same cassette was inserted into BamHI-digested pCl/1GAL4/650 to obtain plasmids GAP3 and GAP4, where GAP3 has the GAPDH promoter distal from the GAL4 regulator region and the long pBR322 sequence and GAP4 has the GAPDH promoter adjacent to the GAL4 regulator region, which is adjacent to the long pBR322 sequence.

Figure 1:
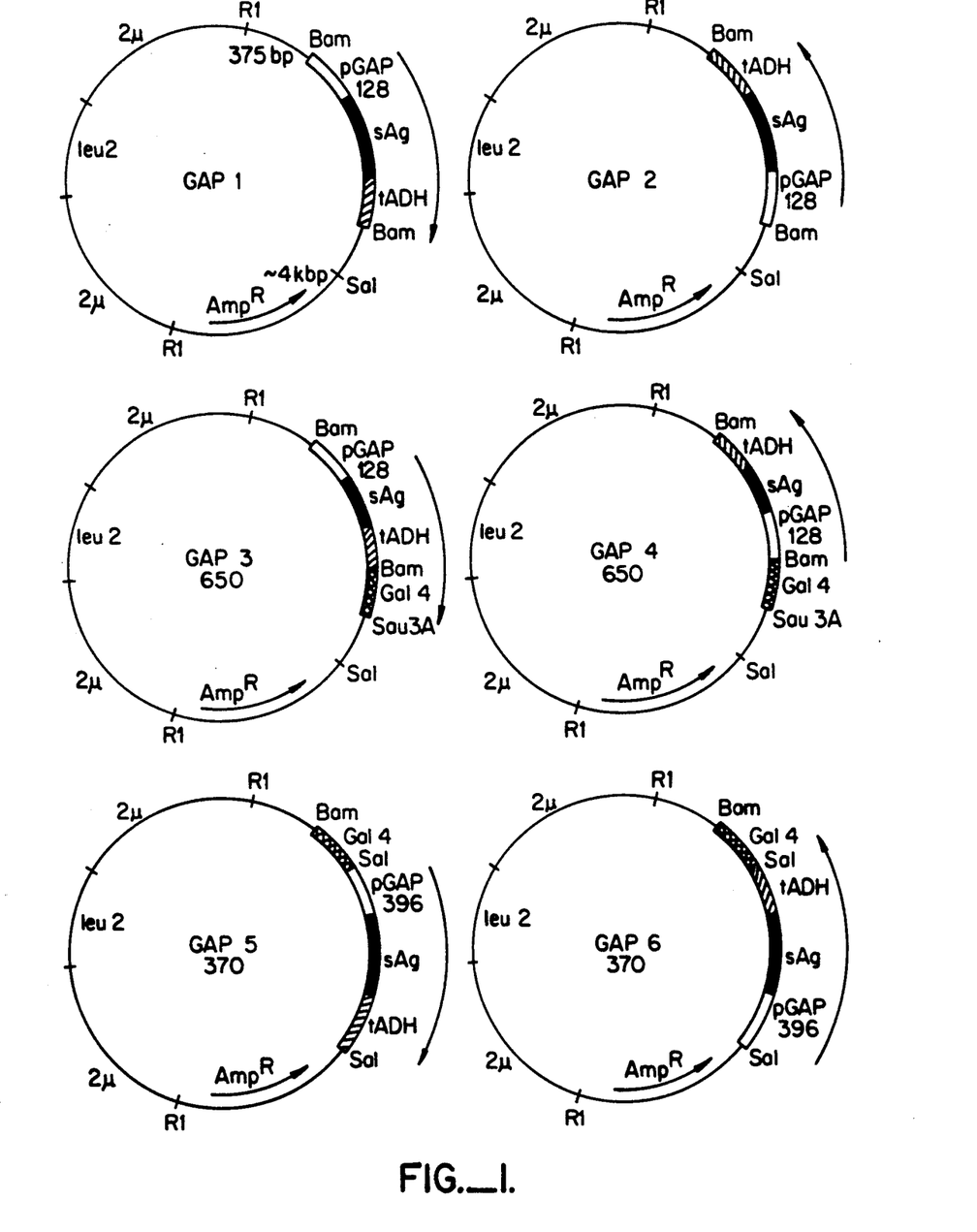
FIG. 1 is a diagrammatic view of plasmids GAP1–6.

Plasmids GAP5 and GAP6 were isolated as follows. Plasmid plot5pGAP396 was digested with SalI and TaqI and a fragment containing 9 bp of the plot5 polylinker sequence and the GAPDH promoter sequence extending from about −385 to −26 bp was isolated. An approximately 130 bp TaqI-XbaI fragment including −25 to −1 bp of the GAPDH promoter and +1 to +93 bp of the sAg gene was obtained from pHBS6LGAPsAgtADH. A 1.1 kb XbaI-SalI fragment containing the 3'-portion of the sAg gene and the ADH terminator as well as 6 bp of plot5 polylinker sequence was obtained from plasmid plot5sAgtADH (described below—Pyruvate Kinase Promoter). These three fragments were ligated, digested with SalI and then cloned into SalI-digested pCl/1GAL4/370. GAP5 has the GAPDH promoter region adjacent to the GAL4 regulator region, which is proximal to the short pBR322 sequence, and GAP6 has the GAPDH promoter region distal from the GAL4 regulator region and proximal to the long pBR322 sequence (see FIG. 1).

Pyruvate Kinase Promoter

Plasmid pHBS6Pyk containing the sAg gene under the transcriptional regulatory control of the Pyk promoter was obtained by cloning a 4.4 kb insert of yeast genomic DNA in pBR322 containing the Pyk gene and 911 nucleotides of 5'-untranslated region, and digestion of this plasmid pPyk9.1.1 with XbaI. After making the ends blunted-ended, the linear fragment was digested with BamHI providing a 912 bp BamHI-blunt fragment containing the Pyk promoter and 8 bases from the Pyk coding region. This fragment was inserted into the plasmid pHBS6, which had been digested with NcoI, blunt-ended and digested with BamHI. The plasmid pHBS6Pyk was totally digested with EcoRI, to obtain a fragment including the sAg gene and a portion of the Pyk promoter region. The fragment was made blunt-ended with the Klenow fragment and dNTPs, followed by ligation to BamHI linkers, digested with XbaI, which is internal to the sAg gene, the XbaI terminus made blunt-ended with the Klenow fragment and dNTPs, followed by digestion with BamHI, to provide a 580 bp BamHI-blunt-ended (XbaI) fragment. The plasmid plot5 was digested with EcoRI, made bluntended, digested with BamHI and treated with alkaline phosphatase and the two fragments joined to provide plasmids plot5PyksAg51 and plot5PyksAg.57. The two differ in that the BamHI site of the latter was not regenerated during cloning, possibly as a consequence of minimal nuclease contamination (digestion).

plot5 was treated as previously described (EcoRI digestion, blunt-ended, BamHI digestion and treatment with alkaline phosphatase) and joined to a 1.1 kb fragment obtained by digestion of pPGT16-3 with XbaI, followed by blunt ending, followed by digestion with BamHI and gel isolation. This fragment was introduced into plot5 to provide the plasmid plot5sAgtADH. Again the BamHI site in this plasmid was not regenerated, presumably due to digestion by contaminating nuclease.

Plasmids Pyk1 and Pyk2 were prepared as follows. Plasmid plot5PyksAg51 was digested with BamHI, then with XbaI, and an approximately 580 bp fragment containing about 480 bp of Pyk promoter and 93 bp of the 5'-end of the sAg gene was gel isolated. A 1.1 kb XbaI-SalI fragment containing the 3'-portion of the sAg gene, the ADH terminator and about 6 bp of the plot5 polylinker was isolated from plot5AgtADH. These two fragments were ligated, digested with BamHI and SalI and then cloned into plasmid pCl/1, which had been cleaved with BamHI and SalI and treated with alkaline phosphatase, to yield plasmid Pyk1. Plasmid Pyk2 was prepared similarly but the 580 bp SalI-XbaI, Pyk promoter/HBsAg gene 5'-end fusion fragment was isolated from plot5PyksAg.57 and included about 6 bp of plot5 polylinker sequence upstream from the promoter region. Also the 1.1 kb XbaI-BamHI fragment containing the 3'-part of the HBsAg gene and the ADH terminator was derived from plasmid pPGT16-3.

Plasmids Pyk3-Pyk6 were prepared as follows. Plasmid plot5PyksAg51 was digested with BamHI, then with XbaI and the about 580 bp fragment containing the Pyk promoter and the 5'-part of the HBsAg gene isolated as above. The 1.1 kb BamHI-XbaI fragment, containing the 3'-portion of the HBsAg gene and ADH terminator, was recovered from pPGT16-3, also as above, and the two fragments ligated, digested with BamHI and inserted with different orientations into the BamHI site of pCl/1GAL4/650 (Pyk3, Pyk4). Plasmids Pyk5 and Pyk6 were prepared similarly except that the SalI-XbaI fragment containing the Pyk promoter and 5'-end of the sAg gene was isolated from plot5PyksAg.57 and the XbaI-SalI sAg gene 3'-portion/ADH terminator fusion fragment was derived from plot5sAgtADH and thus both fragments included approximately 6 bp of plot5 polylinker sequence. The cassette so formed was then cloned into the SalI site of pCl/1GAL4/370 in opposite orientations.

Figure 2:
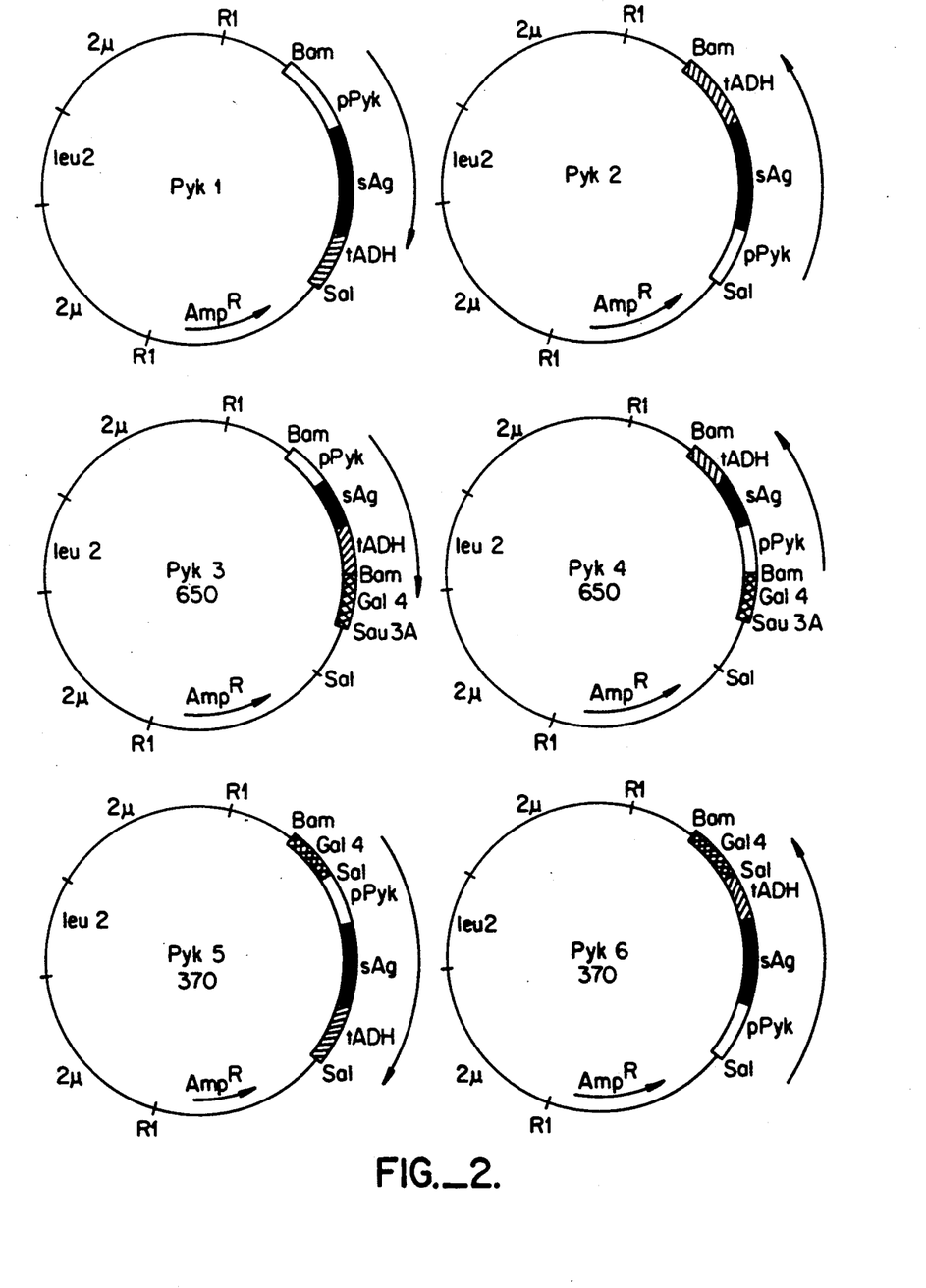
FIG. 2 is a diagrammatic view of plasmids Pyk1–6.

The six plasmids designated Pyk1-6 (see FIG. 2) are distinguished by Pyk1 having the promoter region proximal to the short pBR322 sequence; Pyk2 having the promoter region proximal to the long pBR322 sequence; Pyk3 having the promoter region proximal to the short pBR322 sequence and distal from the GAL4 sequence; while Pyk4 has the promoter region proximal to the GAL4 region, which in turn is proximal to the long pBR322 sequence; Pyk5 has the promoter region proximal to the GAL4 region which is proximal to the short pBR322 sequence; while Pyk6 has a promoter region distal from the GAL4 region and proximal to the long pBR322 sequence.

These plasmids described above were transformed into S. carlsbergensis strain 2150-2-3 (available from Lee Hartwell, University of Washington) under conventional conditions (Hinnen et al., Proc. Natl. Acad Sci. USA (1978) 75:1929-1933). Cultures of 50-150 ml were grown to mid or late log phase in rich media (YEP) under neutral conditions (3% glycerol, 2% lactic acid), and then inducing conditions (+2% galactose), or repressing conditions (+2% glucose) for the final 1-2 generations. After lysis with glass beads and clarification of the supernatants by centrifugation, HBsAg expression was determined as described above. The results for the 12 plasmids are set forth in the following Table 1.

TABLE 1

Expression of HBsAg from Gal Regulated Hybrid Promoters

| Construction | YEP + Glycerol/ Lactic acid μg sAg/mg protein | YEP + Galactose μg sAg/mg protein | YEP + Glucose | Induction (Gal/ glycerol lactic acid) |
|---|---|---|---|---|
| GAP1 | 0.04 | 0.09 | 0.02 | 2.0 |
| GAP2 | 1.65 | 0.8 | 1.4 | 0.5 |
| GAP3 | 0.25 | 0.30 | — | 1.2 |
| GAP4 | 0.10 | 0.75 | — | 7.5 |
| GAP5 | 0.25 | 2.1 | — | 8.4 |
| GAP6 | 1.55 | 1.4 | 1.0 | 0.9 |
| PYK1 | 0.10 | 0.30 | 0.14 | 3.0 |
| PYK2 | 1.65 | 1.4 | 1.1 | 0.85 |
| PYK3 | 0.10 | 0.15 | — | 1.5 |
| PYK4 | 0.10 | 1.0 | 0.05 | 10.0 |
| PYK5 | 0.03 | 1.4 | 0.02 | 47.0 |
| PYK6 | 1.7 | 1.8 | 0.9 | 0.9 |

Construction of pPGAP

A yeast expression vector was prepared called pPGAP having a polyrestriction site linker between the GAPDH terminator and short promoter region. Plasmid plot5pGAP128 was digested with BamHI and TaqI to yield an approximately 390 bp BamHI-TaqI fragment having the −400 to −26 bp of the GAPDH promoter. The BamHI-TaqI fragment was ligated to a synthetic fragment having the following sequence:

```
         PstI         HinfI                    AluI
1        GGTGAATCCGTAATCATGGTCATAGCTGTTTCCTGTGTGAAATTGTTATCCGCTC
         ACGTCCACTTAGGCATTAGTACCAGTATCGACAAAGGACACACTTTAACAATAGGCGAG
         HphI HindII    AluI
60       ACAATTCCACACATTATACGAGCCGATGATTAATTGTCAACAGCTCATTTCAGAATATTT
         TGTTAAGGTGTGTAATATGCTCGGCTACTAATTAACAGTTGTCGAGTAAAGTCTTATAAA EcoRI
120      GCCAGAACCGTTATGATGCGG
         CGGTCTTGGCAATACTACGCCTTAA
```

CGA$_2$TA$_3$(CA)$_3$TA$_3$CA$_3$CACCATG$_3$A$_2$T$_2$CGT$_2$AG$_2$
T$_2$AT$_3$(GT)$_3$AT$_3$GT$_3$GTGGTAC$_3$T$_2$A$_2$GCA$_2$TC$_2$AGCT to provide a BamHI-SalI fragment, which was digested with BamHI and SalI and used to replace the BamHI-SalI fragment of BamHI-SalI digested pBR322 treated with alkaline phosphatase. After ligation, the plasmid pGAPNRS was obtained which was digested with BamHI and SalI to provide a 400 bp BamHI-SalI fragment which was gel isolated. This fragment was ligated to an about 900 bp SalI-BamHI fragment containing the GAPDH terminator region and a short segment of 3' coding region and the resulting 1.4 kb BamHI-BamHI fragment digested with BamHI. The SalI-BamHI GAPDH terminator fragment was obtained by SalI and BamHI digestion of pGAP2, a plasmid prepared by insertion of an about 3.3 kb BamHI fragment containing the GAPDH gene GAP49 (Holland and Holland, supra) into the BamHI site of pBR322. Plasmids pGAP2 and pGAP1 were obtained as follows: A yeast gene library was prepared by inserting fragments obtained after partial digestion of total yeast DNA with restriction endonuclease Sau3A in lambda-phage Charon 28 (Blattner et al., Science (1977) 196:161–169). The phage library was screened with DNA complementary to the yeast GAPDH mRNA and the yeast GAPDH gene from one of these clones was subcloned as either an about 3.3 kb BamHI fragment in the BamHI site of pBR322 (pGAP-2) or as an about 2.1 kb HindIII fragment in the HindIII site of pBR322 (pGAP-1).

pBR322 was digested with EcoRI and SalI, the termini blunt-ended and ligated to BamHI linkers, followed by BamHI digestion and the BamHI-BamHI 3.8 kb fragment gel isolated, recircularized by self-ligation, cloned and designated pBRΔR1-Sal. The 1.4 kb BamHI-BamHI fragment was inserted into the BamHI-digested, alkaline phosphatase treated pBRΔR1-Sal vector to provide the plasmid pPGAP of about 5.3 kb with the orientation in the opposite direction of the amp$^r$.

The plasmid phSOD was prepared as follows:

Molecular Cloning of hSOD cDNA.

Total RNA was prepared from an adult human liver by the guanidinium thiocyanate/lithium chloride method (Cathala et al., DNA (1983) 2:329–335). polyA RNA was used to synthesize double-stranded cDNA (Maniatis et al., Molecular Cloning, 213–242, Cold Spring Harbor, 1982) and this was passed over a Sepharose CL4B column to enrich for cDNAs of greater than 350 bp (Fiddes and Goodman, Nature (1979) 281:351–356). The cDNA was inserted at the PstI site of plot4, a pBR322 derivative having the following sequence replacing the PstI-EcoRI site.

The cDNA insertion employed the oligo-dG:dC tailing method (Maniatis et al., supra). E. coli strain D1210 was transformed with this mixture and transformants selected on L-agar containing 10 μg/ml tetracycline (Kushner, S. R. (1978) In: Genetic Engineering, eds. Boyer, H. B. and Nicosia, S., (Elsevier/North Holland, Amsterdam) p. 17). Plasmid DNA constituting a liver cDNA library was prepared (Maniatis et al., Molecular Cloning, pp. 86–94, Cold Spring Harbor 1982) directly from approximately 62,000 recombinant colonies plated at a density of approximately 3,000 colonies per 9 cm diameter Petri dish.

Isolation of r-hSOD Clones

Strain D1210 was retransformed with the liver cDNA library and about 40,000 clones were grown on nine 14 cm diameter Petri dishes. After transfer of the colonies to nitrocellulose paper and chloramphenicol amplification of plasmid DNA, the cells were lysed and the filters prepared for hybridization (Ish-Horowicz and Burke, Nucleic Acids Research (1981) 9:2989–2998). Oligonucleotide probes were employed for screening by hybridization, with the probes consisting of enzymatically-radiolabeled, chemically-synthesized DNA molecules complementary to the mRNA encoding amino acid residues 19 to 24 of the protein (Jabusch et al., supra.; Barra et al., supra.); the mixture had the following sequences:

```
3' TTA AAA CTT GTT TTT CT 5'
    G   G   C   C   C
``` where all of the indicated possibilities for encoding the peptide sequence were prepared (32-fold degenerate).

The probes were labeled with $^{32}P$ to a specific activity of $1-3 \times 10^8$ cpm/μg and Millipore (0.45 μm) filtered before use. Filters were prehybridized for 6 hrs at 30° C. in 4× SSC, 2× Denhardts's solution, 40 mM sodium phosphate, pH 7.5, 300 μg/ml sonicated salmon testes DNA. Hybridization was for 20 hrs at 30° C. in the same solution containing $2 \times 10^6$ cpm/ml hSOD DNA probe (residues 19-24). Filters were washed in 4× SSC, once for 15 min at r.t. and twice for 15 min at 30° C., blotted dry and autoradiographed with an intensifying screen for 24 hrs at −70° C.

Areas on the master plates that corresponded to duplicate positive signals were picked into L-broth and plasmid DNA prepared by the miniscreen procedure (Maniatis et al., *Molecular Cloning*, 178, 368-369, Cold Spring Harbor 1982). This DNA was cut with PstI and subjected to Southern blot analysis (Southern, *J. Mol. Biol.* (1975) 98:503-517) hybridizing initially with the previous labeled probes (amino acid residues 19-24) and then with additional radiolabeled probes derived from amino acid residues 109-114 and having the following sequences (all possible variations, 72-fold degenerate) present as a mixture:

```
3' CTA GTA ACA TAA TAA CC 5'
    G   G   G   G   G
            T       T
```

One plasmid pool (pSOD1) contained a cDNA insert of 520 bp that hybridized with both probes and after colony purification, plasmid DNA was prepared from this clone and sequenced by the method of Maxam and Gilbert (*Proc. Natl. Acad. Sci. USA* (1977) 74:560-564). The hSOD cDNA clone pSOD1 constitutes the coding region for amino acids 10-153 of hSOD, a single translational stop codon and a 3' untranslated region. Therefore, in the expression vector construct, the base sequence of the region encoding amino acids 1-9 is derived from the published amino acid sequence of hSOD (Jabusch et al., supra; Barra et al., supra) and synthesized chemically as a part of the variable linker segment (see discussion relating to FIG. 3).

Construction of plot5 Derivatives Containing r-hSOD

Figure 3:
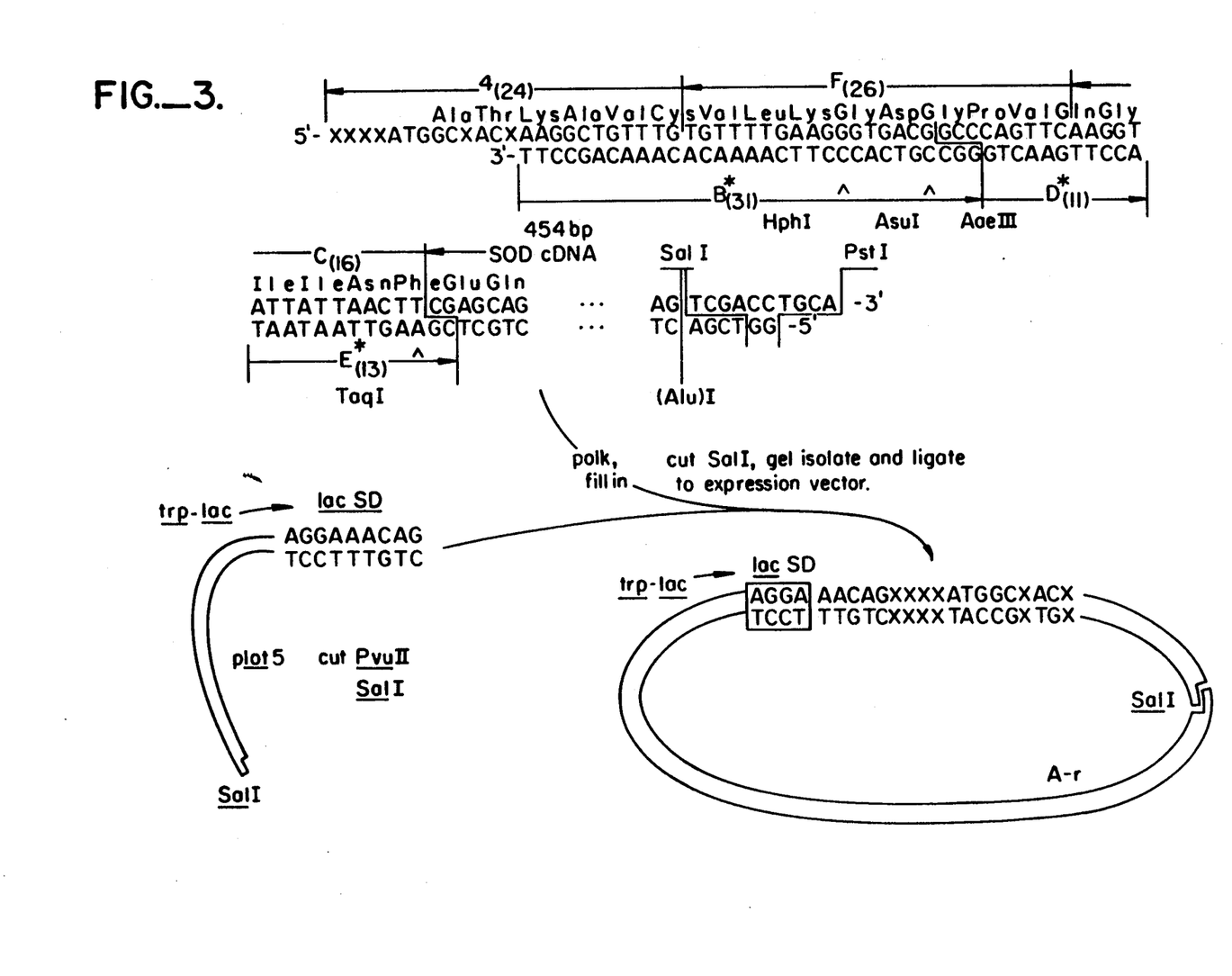
FIG. 3 indicates the DNA linker sequence and a flow diagram showing its use in a construct for hSOD.

The synthetic DNA molecules F(26), C(16), B(31), D(11), E(13) and 4(24) shown in FIG. 3, were synthesized by the phosphoramidite method.

The single strand 4(24) was prepared by using all four bases, at each site where X is indicated. Furthermore, silica was withdrawn from the synthesis of the 24 mer, such that single-stranded 21 mers, 22 mers, and 23 mers are obtained in addition to the 24 mers. After removal from the silica support, the four mixtures are combined in appropriate proportions to provide for equimolar amounts of each of the possible single strands. This mixture was treated as a single product in the subsequent steps.

Molecules F(26), C(16), B(31) and D(11) were mixed together in equimolar amounts and 10 μg phosphorylated using T4 polynucleotide kinase. After phenol-ether extraction, the additional non-phosphorylated synthetic DNA molecules 4(24) and E(13) were added, such that all fragments were equimolar. The equimolar mixture contained 13 μg of DNA in 133 μl of 0.3× kinase buffer.

After annealing by cooling at a uniform rate from 70° C. to 20° C. over 60min, the single strands were ligated together with T4 ligase in 200 μl ligation mix at 14° C. for 4 hrs, phenol-chloroform extracted, ethanol precipitated and the 5'-ends of 4(24) and E(13) phosphorylated using T4 polynucleotide kinase (Maniatis et al., supra). Preparative polyacrylamide gel electrophoresis was used to isolate the completely ligated 53 bp material having 5'- and 3'-overhangs.

The above purified fragment mixture was then ligated to the 460 bp TaqI-PstI segment of the hSOD cDNA as shown in FIG. 3. This segment was itself constructed by isolating the 454 bp TaqI-AluI hSOD fragment, making it flush-ended using Klenow and inserting it into plot5 between its EcoRI and SalI sites which had been similarly made flush-ended. After preparation of plasmid DNA from this recombinant, the 460 bp TaqI-PstI hSOD fragment was isolated by preparative polyacrylamide gel electrophoresis. After extraction and precipitation, the 515 bp fragment resulting from the joining of the synthetic fragment to the 460 bp TaqI-PstI hSOD fragment was blunt-ended (525-528 bp) and then digested with SalI and the resulting 519-522 bp hSOD fragment isolated by polyacrylamide gel electrophoresis. This fragment was then inserted into plot5 which had been digested with PvuII and SalI and then treated with alkaline phosphatase. The resulting plasmids were used to transform strain D1210. Recombinants obtained after transformation of strain D1210 were selected on L-agar containing 100 μg/ml ampicillin to give a set of clones, which were screened for an NcoI site. One was selected and designated phSOD.

Construction of a Yeast Vector for SOD Expression

The plasmid phSOD was digested with NcoI and SalI and a 550 bp fragment obtained, which included 1 nucleotide untranslated at the 5'-terminus and the entire coding region for hSOD. pPGAP was digested with NcoI and SalI followed by treatment with alkaline phosphatase and the SalI-NcoI fragment substituted for the NcoI-SalI fragment in pPGAP to provide pPGAP-SOD. BamHI digestion of pPGAPSOD resulted in a 2 kb fragment which was gel isolated and inserted into the BamHI site of pCl/1 and pCl/1 GAL4/370. These plasmids were transformed into yeast strain 2150-2-3 as described previously, with the results of expression set forth in the following Table 2.

TABLE 2

| Expression of Human SOD in Yeast Strain 2150 | | |
|---|---|---|
| Plasmid | Carbon Source | SOD[2] μg/mg protein |
| pCl/1 | g, L[1] | 0 |
| pCl/1GAPSOD | g, L | 148 |
| pCl/1GALGAPSOD | g, L | 0.4 |

TABLE 2-continued

| Expression of Human SOD in Yeast Strain 2150 | | |
|---|---|---|
| Plasmid | Carbon Source | SOD[2] μg/mg protein |
| | gal | 68 |

[1]All cultures grown in Minus Leucine media with 2% lactic acid, 3% glycerol with or without 2% galactose to late log or early stationary phase.
[2]Determined by RIA.

hSOD levels were measured using a standard radioimmunoassay with iodinated authentic hSOD as standard. Constitutive synthesis from the GAP promoter leads to very high levels of hSOD production, of the order of 10-30% of the total cell protein. The induction with galactose works almost as well, yielding about 7% of the cell protein as hSOD.

Cloning of Alpha-1-antitrypsin

A cDNA library was made from 10 μg of polyA+ RNA isolated from a part of a human liver. This library was prepared by oligo-dT priming of the first cDNA strand and self-priming of the second cDNA strand. The ds cDNA was size fractionated on a Sepharose CL4B column and those molecules greater than 300 bp isolated. This fraction was treated with nuclease S1 and tailed with dCTP, using terminal transferase. The tailed cDNA was annealed to pBR322 which had been digested with pstI and tailed with dGTP. Transformation of $E.$ $coli$ HB101 yielded 60,000 colonies, where greater than 90% of the clones were recombinant.

Two synthetic oligonucleotide probes were used to isolate the alpha-1-antitrypsin ($\alpha_1$-AT) cDNA, the first probe corresponding to amino acid residues 344-350 near the C-terminus of the protein was used to probe 5,000 colonies and the second probe, corresponding to amino acid residues $-23$ to $-17$ (+1 being the first nucleotide of the first codon of the mature $\alpha_1$-AT) of the signal peptide, was used to probe 25,000 colonies. The probe sequences were taken from the partial nucleotide sequence described by Kurachi et al., $Proc.$ $Natl.$ $Acad.$ $Sci.$ $USA$ (1981) 78:6826; Leicht et al., $Nature$ (1982) 297:655). Approximately 3% of the colonies hybridized to the C-terminal probe and four hybridized to the N-terminal probe. The four N-terminal clones and 12 C-terminal clones were isolated and subjected to restriction analysis. From these, three overlapping clones which cover the entire cDNA were subjected to further study and were used to construct the full-length cDNA clone.

The entire sequence of a composite full length cDNA derived from the three plasmids is as follows:

```
                                                           -24
                                                        Met Pro Ser Ser
                                    GGGGGGGGGGGAGGGTAATCGACA ATG CCG TCT TCT

-20                                    -10                                     -1
Val Ser Trp Gly Ile Leu Leu Leu Ala Gly Leu Cys Cys Leu Val Pro Val Ser Leu Ala
GTC TCG TGG GGC ATC CTC CTG CTG GCA GGC CTG TGC TGC CTG GTC CCT GTC TCC CTG GCT

1 Glu Asp Pro Gln Gly Asp Ala Ala Gln Lys Thr Asp Thr Ser His His Asp Gln Asp His
 1 GAG GAT CCC CAG GGA GAT GCT GCC CAG AAG ACA CAT ACA TCC CAT CAT GAT CAG GAT CAC
       - - - - - BamHI

21 Pro Thr Phe Asn Lys Ile Thr Pro Asn Leu Ala Glu Phe Ala Phe Ser Leu Tyr Arg Gln
61 CCA ACC TTC AAC AAG ATC ACC CCC AAC CTG GCT GAG TTC GCC TTC AGC CTA TAC CGC CAG

41 Leu Ala His Gln Ser Asn Ser Thr Asn Ile Phe Phe Ser Pro Val Ser Ile Ala Thr Ala
121 CTG GCA CAC CAG TCC AAC AGC ACC AAT ATC TTC TTC TCC CCA GTG AGC ATC GCT ACA GCC

61 Phe Ala Met Leu Ser Leu Gly Thr Lys Ala Asp Thr His Asp Glu Ile Leu Glu Gly Leu
181 TTT GCA ATG CTC TCC CTG GGG ACC AAG GCT GAC ACT CAC GAT GAA ATC CTG GAG GGC CTG

81 Asn Phe Asn Leu Thr Glu Ile Pro Glu Ala Gln Ile His Glu Gly Phe Gln Glu Leu Leu
241 AAT TTC AAC CTC ACG GAG ATT CCG GAG GCT CAG ATC CAT GAA GGC TTC CAG GAA CTC CTC

Arg(a,c)                                              Asp Gly(c)
101 His Thr Leu Asn Gln Pro Asp Ser Gln Leu Gln Leu Thr Thr Gly Asn Gly Leu Phe Leu
301 CAT ACC CTC AAC CAG CCA GAC AGC CAG CTC CAG CTG ACC ACC GGC AAT GGC CTG TTC CTC

121 Ser Glu Gly Leu Lys Leu Val Asp Lys Phe Leu Glu Asp Val Lys Lys Leu Tyr His Ser
361 AGC GAG GGC CTG AAG CTA GTG GAT AAG TTT TTG GAG GAT GTT AAA AAG TTG TAC CAC TCA

141 Glu Ala Phe Thr Val Asn Phe Gly Asp Thr Glu Glu Ala Lys Lys Gln Ile Asn Asp Tyr
421 GAA GCC TTC ACT GTC AAC TTC GGG GAC ACC GAA GAG GCC AAG AAA CAG ATC AAC GAT TAC

161 Val Glu Lys Gly Thr Gln Gly Lys Ile Val Asp Leu Val Lys Glu Leu Asp Arg Asp Thr
481 GTG GAG AAG GGT ACT CAA GGG AAA ATT GTG GAT TTG GTC AAG GAG CTT GAC AGA GAC ACA

181 Val Phe Ala Leu Val Asn Tyr Ile Phe Phe Lys Gly Lys Trp Glu Arg Pro Phe Glu Val
541 GTT TTT GCT CTG GTG AAT TAC ATC TTC TTT AAA GGC AAA TGG GAG AGA CCC TTT GAA GTC

Ala(b)
201 Lys Asp Thr Glu Glu Glu Asp Phe His Val Asp Gln Val Thr Thr Val Lys Val Pro Met
601 AAG GAC ACC GAG GAA GAG GAC TTC CAC GTG GAC CAG GTC ACC ACC GTG AAG GTG CCT ATG
                                                      - - - - - - BstEII

221 Met Lys Arg Leu Gly Met Phe Asn Ile Gln His Cys Lys Lys Leu Ser Ser Trp Val Leu
661 ATG AAG CGT TTA GGC ATG TTT AAC ATC CAG CAC TGT AAG AAG CTG TCC AGC TGG GTG CTG
```

-continued

```
              Asn(c)
241 Leu Met Lys Tyr Leu Gly Asn Ala Thr Ala Ile Phe Phe Leu Pro Asp Glu Gly Lys Leu
721 CTG ATG AAA TAC CTG GGC AAT GCC ACC GCC ATC TTC TTC CTG CCT GAT GAG GGG AAA CTA

261 Gln His Leu Glu Asn Glu Leu Thr His Asp Ile Ile Thr Lys Phe Leu Glu Asn Glu Asp
781 CAG CAC CTG GAA AAT GAA CTC ACC CAC GAT ATC ATC ACC AAG TTC CTG GAA AAT GAA GAC
                                       - - - - - - EcoRV

281 Arg Arg Ser Ala Ser Leu His Leu Pro Lys Leu Ser Ile Thr Gly Thr Tyr Asp Leu Lys
841 AGA AGG TCT GCC AGC TTA CAT TTA CCC AAA CTG TCC ATT ACT GGA ACC TAT GAT CTG AAG

Val(a,c)
301 Ser Ile Leu Gly Gln Leu Gly Ile Thr Lys Val Phe Ser Asn Gly Ala Asp Leu Ser Gly
901 AGC ATC CTG GGT CAA CTG GGC ATC ACT AAG GTC TTC AGC AAT GGG GCT GAC CTC TCC GGG

321 Val Thr Glu Glu Ala Pro Leu Lys Leu Ser Lys Ala Val His Lys Ala Val Leu Thr Ile
961 GTC ACA GAG GAG GCA CCC CTG AAG CTC TCC AAG GCC GTG CAT AAG GCT GTG CTG ACC ATC

341 Asp Glu Lys Gly Thr Glu Ala Ala Gly Ala Met Phe Leu Glu Ala Ile Pro  Met Ser  Ile
1021 GAC GAG AAA GGG ACT GAA GCT GCT GGG GCC ATG TTT TTA GAG GCC ATA CCC  ATG TCT  ATC

361 Pro Pro Glu Val Lys Phe Asn Lys Pro Phe Val Phe Leu Met Ile Glu Gln Asn Thr Lys
1081 CCC CCC GAG GTC AAG TTC AAC AAA CCC TTT GTC TTC TTA ATG ATT GAA CAA AAT ACC AAG
                                            - - - - - - AvaI

381 Ser Pro Leu Phe Met Gly Lys Val Val Asn Pro Thr Gln Lys OC
1141 TCT CCC CTC TTC ATG GGA AAA GTG GTG AAT CCC ACC CAA AAA TAA CTGCCTCTCGCTCCTCAAC
                                                                - - - - HinfI AAT CCC ACC CAA AAA TAG
                                GGG TGG GTT TTT ATC AGCT
                                                     - - - - SalI 1201 CCCTCCCCTCCATCCCTGGCCCCCTCCCTGGATGACATTAAAGAAGGGTTGAGCTGGAAAAAAAAAAAAAAAAA
AAAAA
```

The above sequence was determined using the dideoxy sequencing method of Sanger et al., *Proc. Natl. Acad. Sci. USA* (1977) 74:5463, in the M13 vectors of Messing et al., *Nucleic Acids Res.* (1981) 9:309. The differences at the nucleotide and amino acid level from the published cDNA sequences are shown.

Construction of the full length clone for expression of yeast began with three fragments isolated from cDNA clones: 1) a 630 bp BamHI-BstEII fragment; 2) a 450 bp BstEII-AvaI fragment; and 3) an 85 bp AvaI-HinfI fragment. A synthetic adapter was employed having the following sequence:

$$A_2TC_3AC_3A_5TAG$$
$$G_3TG_3T_5ATCAGCT$$

Approximately two pmoles of fragments 1 and 2 were ligated together and after removal of the ligase, digested with BamHI and AvaI. Fragment 3 and the synthetic adapter were ligated and digested with AvaI and SalI and the two resulting fragment mixtures were ligated followed by digestion with BamHI and SalI. Fragments migrating upon electrophoresis in the region of about 1000-1400 bp were isolated and cloned by substitution into BamHI and SalI digested and alkaline phosphatase treated pBR322. The resulting plasmid is referred to as pATi.

Plasmid pPGAP was digested with NcoI, followed by blunt-ending, followed by SalI digestion and treatment with alkaline phosphatase. The NcoI-SalI fragment was substituted with an approximately 1250 bp blunt-ended (BamHI)-SalI fragment obtained from plasmid pATi, by BamHI digestion, blunt ending, and SalI digestion. This was inserted into the pPGAP vector to produce the plasmid pGAPATi, a 6.6 kb plasmid, which was digested with NcoI and BamHI and a 2.3 kb NcoI-BamHI fragment obtained having the $\alpha_1$-AT gene and the GAPDH terminator and approximately 400 bp BamHI-NcoI fragment obtained having the GAPDH promoter. These fragments were ligated together and inserted into the BamHI site of pCl/1. The plasmids pCl/1GAPATi8 and pCl/1GAPATi9 were obtained with the orientation of expression clockwise in the former and counterclockwise in the latter, with amp$^r$ being in the counterclockwise direction. These plasmids were transformed in *S. cerevisiae* AB103 (A.T.C.C. No. 20658, deposited Jan. 5, 1983) by standard methods, selecting for leucine prototrophy and grown as described above. Yeast extracts were prepared by lysis with glass beads and the $\alpha_1$-AT activity determined by inhibition of human leukocyte elastase.

Assays contained in 1 ml:0.1–0.2 human leukocyte elastase (HLE); 0.1 mM MeO-Suc-Ala-Ala-Pro-Val-p-nitroanilide (Beatty et al., *J. Biol. Chem.* (1980) 255:3931); 50 mM Tris, pH 8, 0.5M NaCl, and the indicated amounts of yeast extract or human $\alpha_1$-AT. Assays were initiated by the addition of elastase, incubated at 28° C. for 15min, terminated by the addition of 100 μl of 8N acetic acid and the absorbance at 410 nm determined. Typical results are shown in the following Table 3.

TABLE 3

| Plasmid | Strain | Amt. Extract (μl) | Amt. HLE (μg) | Amt. Protein (μg) | % Elastase Activity | % $\alpha_1$-AT* |
|---|---|---|---|---|---|---|
| pCl/1GAPATi8 | AB103 | 5.0 | 0.1 | 50.0 | 40 | 0.17 |

TABLE 3-continued

| Plasmid | Strain | Amt. Extract (μl) | Amt. HLE (μg) | Amt. Protein (μg) | % Elastase Activity | % α₁-AT* |
|---|---|---|---|---|---|---|
| | | 10.0 | 0.1 | 100.0 | 26 | 0.11 |
| pCl/1GAPATi9 | AB103 | 0.25 | 0.1 | 2.3 | 89 | 0.7 |
| | | 1.0 | 0.1 | 9.1 | 26 | 1.2 |
| pCl/1GAPATi9 | AB110 | 0.2 | 0.2 | 2.9 | 39 | 6.1 |
| | | 0.4 | 0.2 | 5.8 | 14 | 4.3 |

*Calculation based upon the Mol. wt. of HLE (29kD), the amount of protein added and the degree of inhibition.

The above data demonstrate that plasmids having the orientation of the expression cassette in the counter-clockwise orientation, the promoter proximal to the long sequence of pBR322, make 10–20 times more $\alpha_1$-AT than the same cassette in the other orientation.

Yeast Strain AB110

Yeast strain 2150-2-3 was crossed with a yeast strain AB103 transformant containing pCl/1GAPATi9. The diploids were sporulated and the tetrads disected. Strains were maintained on leucine selective plates in order to ensure maintenance of the plasmid, since the parents are auxotrophs. A series of colonies were screened for their genotype with respect to a number of markers. The most vigorous strains were selected and cultures grown on leucine selective media. The best strain was designated AB110 (pCl/1GAPATi9), gave 6–7.5% of the total cell protein as $\alpha_1$-AT as shown in the above Table 3. The strain AB110 has the following genotype: Mat$\alpha$, ura3-52, leu2-04 or both leu2-3 and leu2-112, pep4-3, his4-580 (cir°).

Phosphate Induction

Plasmid pPGT80 was digested with BamHI, the ends blunt-ended, followed by digestion with XbaI and the 500 bp fragment containing the GAPDH promoter and 5′-end of the sAg gene isolated.

The PHO5 gene was isolated from a yeast genomic library employing an oligonucleotide probe 5′-GGCACTCACACGTGGGACTAG-3′ derived from the published partial sequence (Meyhack et al., The EMBO Journal (1982) 1:675–680). A subfragment of this clone containing 550 bp of the 5′-untranslated region and approximately 80 bp of coding sequence was subcloned as a BamHI-SalI substitution in pBR322 to provide pPHO5. This fragment has the sequence 5′-ATGTTTAAA-3′, encoding the first three amino acids, the second and third codons specifying an AhaIII site. The plasmid pHBS6 was digested with NcoI, blunt-ended, followed by digestion with BamHI and treatment with alkaline phosphatase. The PHO5 promoter region was obtained by digesting the pPHO5 plasmid with AhaIII, resecting the resulting fragment with Bal31 for a short time, followed by digestion with BamHI and isolation of a 500–550 bp BamHI blunt-ended fragment. This fragment was employed for substitution of the NcoI-BamHI fragment from pHBS6 and was screened for regeneration of the NcoI restriction site to provide plasmid pHBS6PHO5/1.

Plasmid pHBS6PHO5/1 was digested with BstEII which cleaves at position −175 in the PHO5 promoter. This molecule was blunt-ended, digested with SalI and the 650 bp fragment having the 5′-portion of the promoter domain, containing 275 bp of pBR322 and 375 bp of the PHO5 promoter region isolated. This fragment was ligated with the blunt-ended (BamHI)-XbaI fragment obtained from digestion of pPGT80 with BamHI, blunt ending, followed by XbaI digestion. After digesting the ligated fragment with SalI and XbaI, the resulting fragment was then substituted into pPGT16-3 which had been digested with SalI and XbaI and treated with alkaline phosphatase. The resulting plasmid pPHO5PGT80 had a cassette comprising the PHO5 regulatory region, the GAPDH promoter, the sAg gene and the ADH terminator. This cassette was excised from the plasmid by BamHI digestion, whereby a 1.8 kb BamHI-BamHI fragment was gel isolated and ligated into the BamHI site of BamHI digested and alkaline phosphatase treated pCl/1 to provide plasmids PHO5-GAP1 and PHO5GAP2 where the PHO5 was distal and proximal to the long pBR322 sequence, respectively.

The two plasmids were transformed into yeast strain 2150-2-3 as described above and grown in rich media as described above for 8 to 10 generations in either high (7 mM) or low (0.2 mM) phosphate. Samples were harvested in late log phase and HBsAg determined as described previously. The results are shown below in Table 4.

TABLE 4

| Regulation of HBsAg Production in Yeast using a Hybrid PHO5/GAPDH Promoter. | | | |
|---|---|---|---|
| | High Phosphate (7 mM) | Low Phosphate (0.2 nM) | Induction |
| Construction | (sAg μg/mg protein) | | low/high |
| PHO5GAP-1 | 0.08 | 0.95 | 12.0 |
| PHO5GAP-2 | 0.27 | 0.40 | 1.5 |

From the above results, it is evident that effective regulation with phosphate is obtained, with one orientation being superior to the other.

It is evident from the above results, that highly efficient expression can be obtained, either constitutive or regulated, by providing for truncated promoter regions of yeast glycolytic enzyme gene promoters, employing the 3′ domain proximal to the coding region of the gene in conjunction with a 5′-portion or second domain of the promoter region of a yeast gene subject to inducible regulation by a nutrient, e.g., carbon source or phosphate, temperature, or other externally controllable source or condition. Alternatively, the second domain may be replaced by prokaryotic sequences of at least about 1 kb or greater, which provide for constitutive enhancement in the absence of the second domain of the promoter region. Thus, a wide variety of genes exogenous to yeast may be expressed in high yield in high percentages of the total protein of the yeast host.

Although the foregoing invention has been described in some detail by way of illustration and example for purposes of clarity of understanding, it will be obvious that certain changes and modifications may be practiced within the scope of the appended claims.

What is claimed is:

1. A DNA construct useful for enhanced constitutive expression of foreign DNA in a yeast host, said DNA construct comprising the following domains which are operably linked in the direction of transcription and directly fused without intervening sequences:
- (a) a distal enhancing domain comprising a portion of the 4 Kb EcoRI-BamHI fragment of pBR322 wherein aid fragment is capable of enhancing constitutive expression of a downstream segment of foreign DNA;
- (b) a proximal promoting domain of less than 600 bp comprising the RNA polymerase binding site and transcription initiation site of the Saccharomyces-derived glyceraldehyde-3-phosphate dehydrogenase (GAPDH) gene promoter;
- (c) an insertion domain having at least one restriction site; and
- (d) a termination domain comprising a transcriptional terminator recognized by said yeast host.

2. The DNA construct of claim 1 further comprising a segment of foreign DNA inserted into said insertion domain.

3. A plasmid vector comprising the DNA construct of claim 2 wherein said plasmid vector is capable of replication in a yeast host cell.

4. A modified yeast cell containing the DNA construct of claim 2 wherein said yeast cell constitutively expresses said segment of foreign DNA.

5. A method of constitutive production of a foreign polypeptide from the modified yeast host cell of claim 4 comprising growing the modified yeast cell in culture and purifying said foreign polypeptide.

6. The method of claim 5 wherein aid foreign polypeptide is encoded by a gene encoding a protein chosen from the group consisting of Hepatitis B surface antigen, superoxide dismutase, and alpha$_1$-antitrypsin.

7. The DNA construct of claim 2 wherein:
- a) said distal enhancing domain is substantially all of said 4 Kb EcoRI-BamHI fragment of pBR322; and
- b) said proximal promoting domain contains basepairs $-400$ to $-1$ of the promoter of said GAPDH gene.

8. The DNA construct of claim 1 wherein:
- a) said distal enhancing domain is substantially all of said 4 Kb EcoRI-BamHI fragment of pBR322; and
- b) said proximal promoting domain contains basepairs $-385$ to $-1$ of the promoter of said GAPDH gene.

* * * * *

UNITED STATES PATENT AND TRADEMARK OFFICE
CERTIFICATE OF CORRECTION

PATENT NO. : 5,089,398
DATED : February 18, 1992
INVENTOR(S) : Rosenberg, et al

It is certified that error appears in the above-identified patent and that said Letters Patent is hereby corrected as shown below:

On the title page: should read at section 63:

--[63]: This application is a continuation of application No. 07/073,381 filed July 13, 1987, now abandoned, which is a continuation of application No. 06/609,540 filed May 11, 1984, now abandoned, which is a continuation-in-part of application No. 06/468,589 filed February 22, 1983, now abandoned.--

Column 1, lines 6-9  should read

--This application is a continuation of application No. 07/073,381 filed July 13, 1987, now abandoned, which is a continuation of application No. 06/609,540 filed May 11, 1984, now abandoned, which is a continuation-in-part of application No. 06/468,589 filed February 22, 1983, now abandoned.--

Signed and Sealed this

Twentieth Day of June, 2000

*Attest:*

Q. TODD DICKINSON

*Attesting Officer*     *Director of Patents and Trademarks*